United States Patent [19]
Akiba et al.

[11] Patent Number: 5,810,718
[45] Date of Patent: Sep. 22, 1998

[54] COUPLER STRUCTURE FOR TUBE UNITS OF ENDOSCOPES

[75] Inventors: Haruo Akiba; Seiki Yamaguchi, both of Omiya, Japan

[73] Assignee: Fuji Photo Optical Co., Ltd., Omiya, Japan

[21] Appl. No.: 18,306

[22] Filed: Feb. 3, 1998

[30] Foreign Application Priority Data

Feb. 14, 1997 [JP] Japan ..................................... 9-047340
Mar. 17, 1997 [JP] Japan ..................................... 9-084451

[51] Int. Cl.$^6$ ......................................................... A61B 1/00
[52] U.S. Cl. ............................................. 600/153; 600/156
[58] Field of Search .................................... 600/152, 153, 600/156, 159

[56] References Cited

U.S. PATENT DOCUMENTS

| | | | |
|---|---|---|---|
| 4,732,139 | 3/1988 | Kawashima et al. | 600/153 |
| 4,815,450 | 3/1989 | Patel | 600/152 |
| 5,320,091 | 6/1994 | Grossi et al. | 600/156 |
| 5,343,854 | 9/1994 | Katsurada | 600/152 |
| 5,489,256 | 2/1996 | Adair | 600/156 |
| 5,630,782 | 5/1997 | Adair | 600/156 |
| 5,725,478 | 3/1998 | Saad | 600/156 |
| 5,728,045 | 3/1998 | Komi | 600/156 |

*Primary Examiner*—Paul J. Hirsch
*Attorney, Agent, or Firm*—Ronald R. Snider

[57] ABSTRACT

A coupler structure for tube units of endoscopes functions to prevent a liquid, etc. remaining in aspiration tubes from adhering or penetrating to or into other tubes, and avoid increasing surplus cleaning and sterilizing works. Aspiration tubes have protruding lengths longer than those of air feeding tubes and water feeding tubes in couplers of an endoscope which is configured to couple a tube unit with a control section by way of a faucet joint and control rings. All these tubes are arranged so as to protrude from wall surfaces. When a positioning key and a key groove which also serve for restricting rotation are to be disposed, this key is configured longer than the aspiration tubes. This coupler structure allows the air feeding tube and the water feeding tube to have been already pulled out when the aspiration tube is pulled out, thereby preventing soiled water, etc. flowing out of the aspiration tubes from adhering to or penetrating into the air feeding tubes and water feeding tubes. The protruding structure also serves for preventing soiled water, etc. from flowing into the tubes.

8 Claims, 6 Drawing Sheets

COUPLER STRUCTURE FOR TUBE UNITS OF ENDOSCOPES

BACKGROUND OF THE INVENTION

This application claims the priority of Japanese Patent Applications No. 9-47340 filed on Feb. 14 and No. 9-84451 filed on Mar. 17, 1997, which are incorporated herein by reference.

FIELD OF THE INVENTION

The present invention relates to a coupler structure for tube units of endoscopes, and more specifically a coupler structure which connects a tube unit to a main unit of an endoscope which has a tube unit configured to allow tubes such as an aspiration tube, an air feeding tube and a water feeding tube to be uncoupled in the tube unit.

DESCRIPTION OF THE PRIOR ART

A conventional electronic endoscope (scope) body, for example, consists of a tip section comprising a CCD (charge coupled device), an insert section, a control section, and a cable which is to be connected to a light source unit and a processor unit. In an endoscope main unit and the cable, there are arranged a light guide, an electric signal line, an air feeding tube and water feeding tube for feeding air and water into the tip section, an aspiration tube for inserting treating implements and aspirating contents of a body to be observed, and so on.

Such an endoscope irradiates an interior of a body to be observed with light emitted from the light source unit by way of the light guide from the tip section, picks up an image of an interior of the body to be observed with the CCD and allows observation of the image through the CCD. This endoscope allows air and water to be fed from the tip section to an observation window, etc. through the air feeding tube and the water feeding tube, and permits inserting treating implements and aspirating or discharging soiled matters, etc. from inside the body to be observed through the aspiration tube.

Since the endoscope is used at sites of medical treatments, it requires cleaning, sterilization and disinfection of the tubes but poses a problem that it does not allow efficient cleaning and disinfection. Speaking concretely, the scope as a whole is long and, when it uses valves which are mechanically opened and closed with an aspiration button, an air feeding button and a water feeding button, the tubes are complicated (partially cut) in a mechanical control section, thereby making it difficult to advance a cleaning brush beyond this section or making it impossible to pass the cleaning brush from the tip section into the cable with a stroke.

Accordingly, it is conventionally necessary to flow cleaning water through the tubes for a long time, so that cleaning works become tedious, and it is necessary to improve the mechanical valve control section so as to allow the cleaning brush to penetrate as deep as possible, so that structures which require cleaning are complicated.

Further, an electronic endoscope cannot be subjected to sterilization treatment using an autoclave or the like, unlike other medical implements since it comprises a CCD as an image pickup device, driving and control circuits for this device, and parts which are cemented to the endoscope with bonding agents. Accordingly, a long time is required for disinfection of the endoscope with a sterilizing liquid.

BRIEF SUMMARY OF THE INVENTION

The present invention has been achieved in view of the problems described above and has a primary object to provide a coupler structure for tube units of endoscopes which is configured so as to facilitate cleaning with a cleaning brush, and can be subjected to a disinfection treatment such as sterilization with an autoclave and prevents liquids, etc. remaining in an aspiration tube from adhering to or penetrating into other tubes.

For facilitating cleaning with a cleaning brush and sterilization with an autoclave to accomplish the object, it is conceivable to uncouple tubes in their courses, for example, at locations in a control section. In other words, cleaning with a cleaning brush can be facilitated by shortening the tubes to be cleaned with a cleaning brush and the sterilization of a tube unit with an autoclave can be facilitated by detaching the tube unit from a section which comprises electrical structures.

Figure 10:
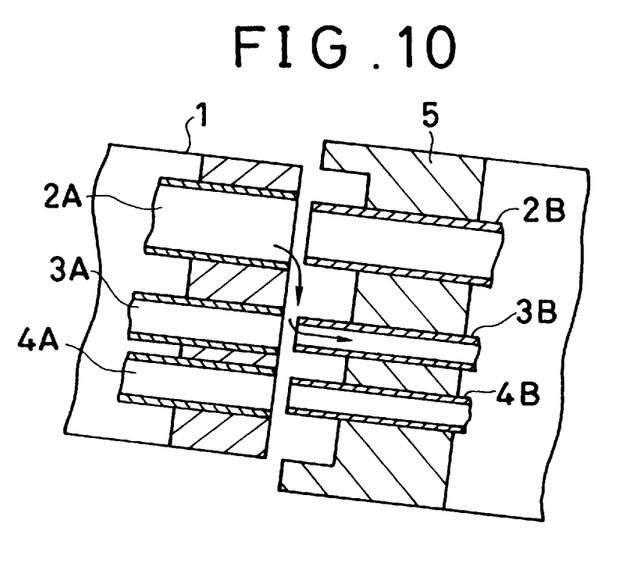
FIG. 10 is a sectional view illustrating another structure conceivable as couplers for endoscopes having discrete tube units.

Couplers of such an endoscope which uses a discrete tube unit have structures exemplified in FIG. 10. In FIG. 10, an aspiration tube 2A, an air feeding tube 3A and a water feeding tube 4A are disposed on a side of an endoscope main unit 1, and an aspiration tube 2B, an air feeding tube 3B, a water feeding tube 4B are disposed so as to protrude on a side of a tube unit 5 so that these tubes are coupled with the tubes 2A, 3A and 4A, respectively.

However, such couplers may allow, at a stage to detach the tube unit 5 from the main unit 1, soiled liquid, etc. dropping from the aspiration tube 2A to adhere to or penetrate into the air feeding tube 3B or the water feeding tube 4B, thereby posing a problem that the air feeding tube 3B and the water feeding tube 4B are soiled unnecessarily. That is, penetration of soiled residue into the tubes 3B and 4B from the aspiration tubes 2A and 2B which are used for introducing treating implements and aspirating the soiled residue from inside a body to be observed is undesirable from a viewpoint of hygiene, and increases surplus works for cleaning and sterilization.

A coupler structure for tube units of endoscopes according to an invention as claimed in claim 1 comprises an endoscope main unit in which various tubes including aspiration tubes are arranged and, a tube unit which has tubes to be connected to the tubes of the main unit and detachably attached to the main unit, and is characterized in that the aspiration tubes have protruding lengths which are longer than those of the other tubes in couplers of the main unit or the tube unit (on a side of either the main unit or the tube unit) so that the aspiration tubes are pulled out last out of the tubes when the tube unit is detached from the main unit. The protruding lengths of the tubes can be adjusted on the side of either the tube unit or the endoscope main unit.

It is preferable to dispose, in the coupler of the endoscope main unit or the tube unit, a positioning member which restricts a rotation and determines a position of the coupler, and is longer than the tubes.

The invention described above allows the aspiration tubes to be pulled out after the air feeding tubes and the water feeding tubes are pulled out, for example, on a side of the tube unit when the coupler is detached, thereby preventing soiled liquid, etc. dropping from the aspiration tube on the side of the endoscope main unit from adhering to or penetrating into the air feeding tube or the water feeding tube. When such a coupler is equipped with a positioning member which restricts rotation, it is possible to allow this member to exhibit a positioning function sufficiently by configuring this member so as to be longest.

A coupler structure according to another invention comprises an endoscope main unit in which various tubes are arranged, a tube unit in which tubes to be connected to the tubes on a side of the main unit are arranged and couplers which detachably couple the tubes on the side of the main unit to the tubes on a side of the tube unit, and is characterized in that the tubes on the sides of the main unit and the tube unit are disposed so as to protrude from wall surfaces of the couplers, and these protruding tubes are coupled with each other.

When aspiration tubes and other tubes are disposed as the various kinds of tubes described above, protruding tips of two tubes in the coupler can be disposed at locations different from protruding tips of the other tubes.

The coupler according to the other invention described above in which the tubes disposed in the couplers protrude from the wall surfaces prevents soiled water, etc. flowing out of tubes from penetrating into the other tubes. It is possible to prevent more completely the penetration of soiled water, etc. by disposing tips of aspiration tubes, for example, so as not to be flush with tips of the other tubes.

When an airtightness maintaining member made of rubber or the like is attached on the side of the tube unit in each of the inventions described above, it is possible to sterilize the airtightness maintaining member and surroundings thereof by sterilizing the tube unit with an autoclave or the like. Sterilization such as autoclaving is not suited for the main unit in which electric parts, etc. are arranged.

Furthermore, it is possible to completely prevent external soiled liquid, etc. from penetrating into the tubes by disposing back flow preventive means in tips of the tubes.

DETAILED DESCRIPTION OF THE PREFERRED EMBODIMENTS

First Embodiment

Figure 1:
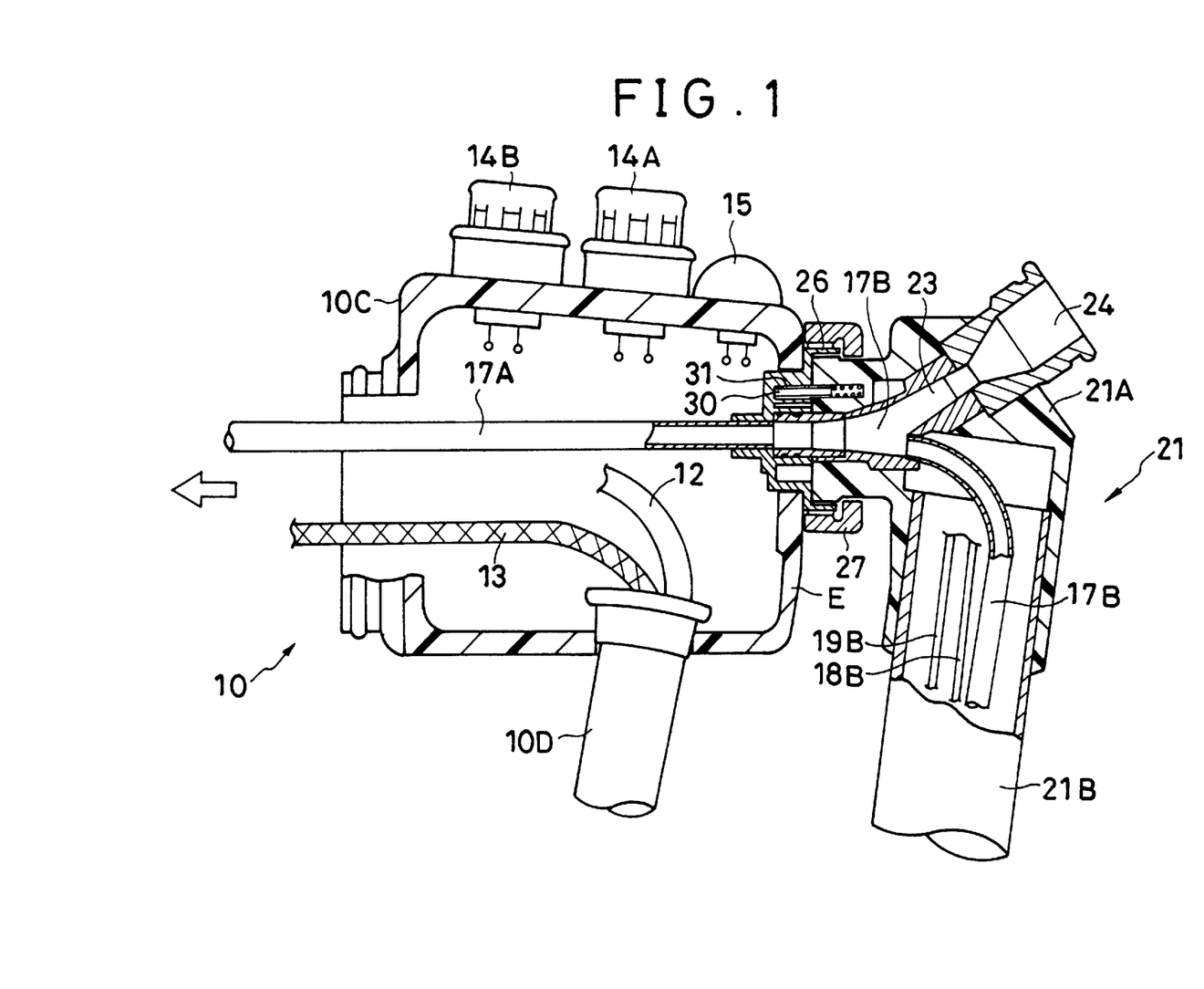
FIG. 1 is a sectional view illustrating a coupler structure for tube units (aspiration tubes in particular) preferred as a first embodiment of the present invention.

FIGS. 1 through 5 show a coupler structure for tube units of endoscopes preferred as a first embodiment of the present invention: FIG. 2(A) being a front view of a coupler on a side of a control section, FIG. 2(B) being a front view of a coupler on a side of a tube unit, FIGS. 1 and 3 being sectional views taken along a I—I line in FIGS. 2(A) and 2(B), and FIG. 4 being a sectional view taken along a II—II line in FIGS. 2(A) and 2(B). In FIG. 1, a tip section comprising a CCD and an insert section (not shown) are disposed in an electronic endoscope 10, and a control section 10C and a first cable 10D are disposed at the back of the insert section as shown in the drawing. This first cable 10D comprises a light guide 12 and a signal line 13 which are laid from the tip section to the control section 10C, and serves for connecting the light guide 12 and the signal line 13 to a light source unit and a processor (image processor) unit, respectively. Accordingly, the endoscope is capable of projecting rays from the tip section and reading out video signals from the CCD.

Disposed on the control section 10C are an aspiration button 14A, an air feeding/water feeding button (two-step switch) 14B, a hard copy button 15, an angle knob (not shown), etc. which are electric switches. The endoscope 10 is equipped with an solenoid valve unit as an independent unit which performs aspiration and air/water feeding operations by opening and closing solenoid valves with inputs given as operation signals from the aspiration button 14A and the air feeding/water feeding button 14B.

Figure 2A:
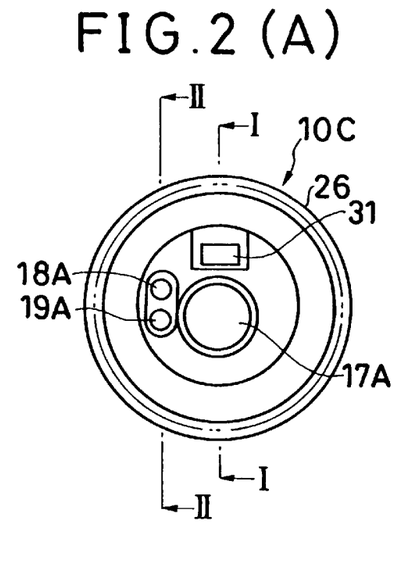
FIG. 2(A) is a front view illustrating a configuration of a coupler on a side of a control section shown in FIG. 1.
Figure 2B:
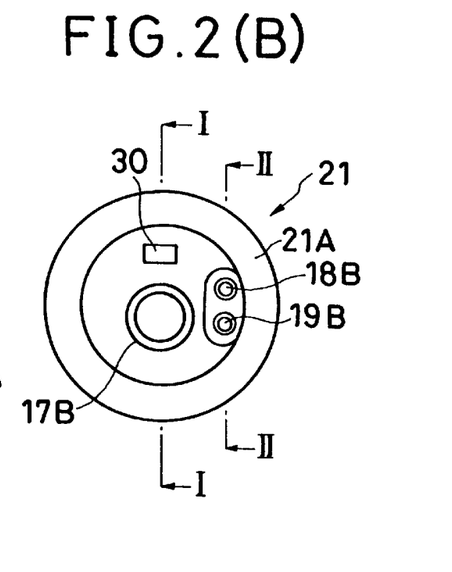
FIG. 2(B) is a front view illustrating a configuration of a coupler on a side of a tube unit shown in FIG. 1.

Further, various tubes are arranged in the control unit 10C. An aspiration tube 17A is arranged at a center of the coupler as shown in FIG. 2(A), and an air feeding tube 18A and a water feeding tube 19A are disposed beside the aspiration tube 17A. A tube unit 21 is detachably attached to a rear end E of the control section 10C.

This tube unit 21 is composed of a support section 21A and a second cable 21B for connection to the solenoid valve unit described above, and comprises an aspiration tube 17B, an air feeding tube 18B and a water feeding tube 19B which are to be coupled with the tubes 17A, 18A and 19A on a side of the control section 10C (main unit). These tubes 17B, 18B and 19B are led to the solenoid valve unit. A forceps port 24 is disposed as an introduction port for treating implements in the aspiration tube 17B by way of a branch tube 23.

Figure 3:
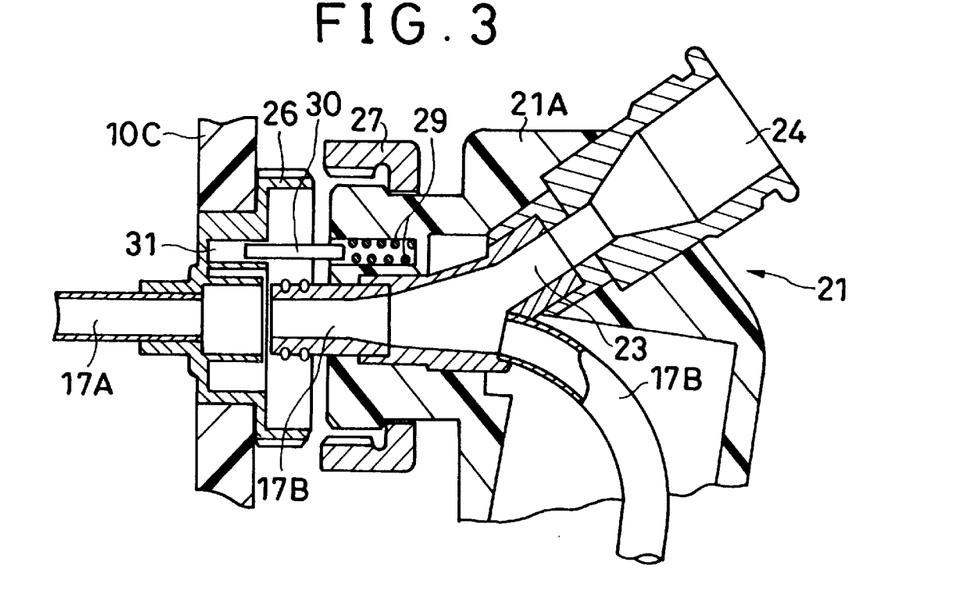
FIG. 3 is a sectional view taken along a I—I line in FIGS. 2(A) and 2(B) for illustrating a configuration of aspiration tubes when the coupler shown in FIG. 1 is detached.

Furthermore, the couplers of the control section 10C and the tube unit 21 are configured as thread fixing type couplers. Speaking concretely, a faucet joint 26 which has a male thread on its circumference is attached to the rear end E of the control section 10C, and a rotatable control ring (rotating ring) 27 which has a female thread on its inner circumference is disposed over a support portion 21A of the tube unit 21 as shown in FIG. 3, etc. Accordingly, the tube unit 21 can be connected and fixed to the control section 10C by screw coupling the control ring 27 over the faucet joint 26.

Moreover, a positioning member which restricts rotation and determines position of the couplers is disposed in the coupler of the first embodiment. Speaking concretely, a rectangular bar-like positioning key 30 which is urged by a spring 29 is disposed in the support portion 21A of the tube unit 21 and a key groove 31 is formed in the faucet joint 26 as shown in FIG. 3 so that the tube unit 21 can be coupled smoothly and securely by inserting the positioning key 30 into the key groove 31. This positioning role can be performed by coupling the aspiration tubes 17A and 17B themselves without disposing the positioning key 30 and the key groove 31.

Figure 4:
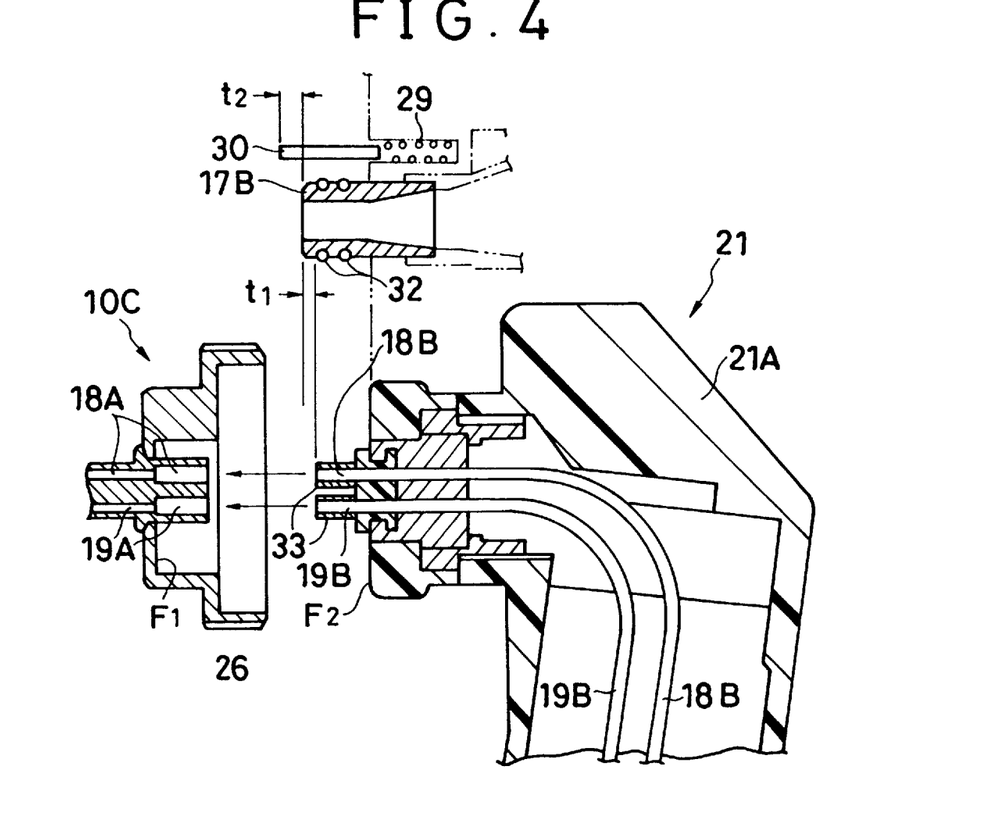
FIG. 4 is a sectional view taken along a II—II line in FIGS. 2(A) and 2(B) for illustrating configurations of an air feeding tube and a water feeding tube when the coupler shown in FIG. 1 is detached.

In the couplers which are structured as described above, the aspiration tube 17B is configured so as to protrude t1 longer than the air feeding tube 18B and the water feeding tube 19B as shown in FIG. 4, and the positioning key 30 is configured so as to protrude t1 longer than the aspiration tube 17B which is urged by the spring 29. Accordingly, the first embodiment prevents soiled liquid, etc. flowing out of the aspiration tube 17A from dropping onto the air feeding tube 18B or the water feeding tube 19B.

The endoscope which is structured as described above has a merit to facilitate cleaning and disinfecting treatment including sterilization with an autoclave, etc. by handling the tube unit 21 separately from the main unit. At a stage to couple the tube unit 21 with the control section 10C, the aspiration tubes 17A and 17B, the air feeding tubes 18A and 18B, and the water feeding tubes 19A and 19B can be coupled with each other smoothly and securely by inserting the positioning key 30 into the key groove 31 as shown in FIG. 3, thereby preventing one of the couplers from rotating, and bending the air feeding tube 18B and the water feeding tube 19B.

Figure 5:
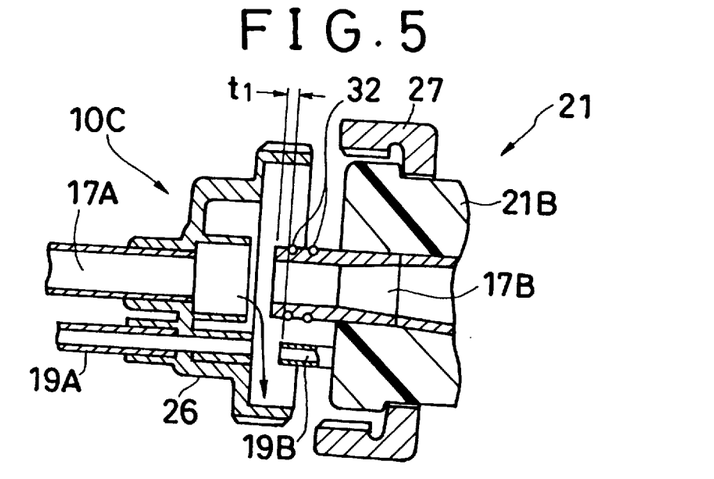
FIG. 5 is a diagram descriptive of relationship of the aspiration tubes and the other tubes for practical detachment of the tube unit.

At a stage to detach the tube unit 21 from the control section 10C by unscrewing the control ring 27 from the faucet joint 26, on the other hand, the air feeding tube 18B and the water feeding tube 19B are pulled out first, and then the aspiration tube 17B is pulled out as shown in FIG. 5. Should soiled water, etc. flow out of the aspiration tube 17A on the side of the control section 10C in the condition shown in the drawing, it does not drop onto, adhere to or penetrate into the air feeding pipe 18B or the water feeding tube 19B which has the shorter protruding length.

In the couplers described above, all the tubes 17A, 17B, 18A, 18B, 19A and 19B are disposed so as to protrude from wall surfaces F1 and F2 as shown in the drawings, and the two air feeding tube 18A and water feeding tube 19A on the side of the control section 10C are formed on a single member so as to protrude therefrom as shown in FIG. 4.

Figure 9:
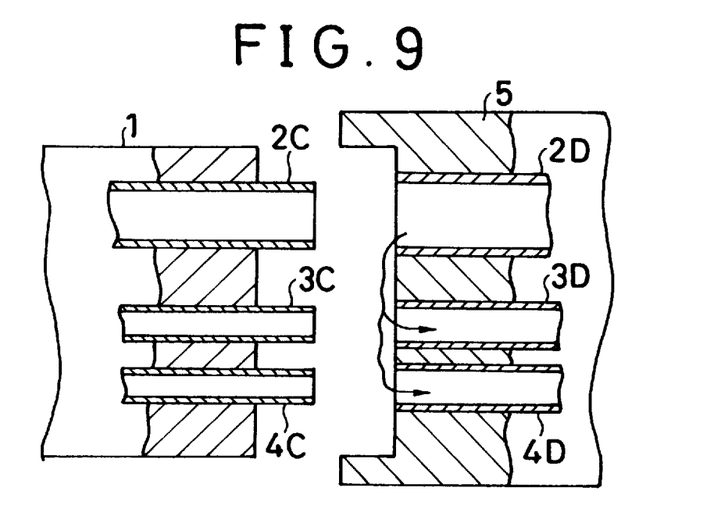
FIG. 9 is a sectional view illustrating a structure conceivable as couplers for endoscopes having discrete tube units.

This structure provides a merit that soiled liquid, etc. does not run along the wall surface and penetrate into the other tubes. Though the endoscope having the discrete type tube unit may have a structure wherein aspiration tubes 2C and 2D, air feeding tubes 3C and 3D, and water feeding tubes 4C and 4D are arranged, for example, as shown in FIG. 9, this structure may allow soiled liquid, etc. remaining in each tube (2A, 2B, 3A, 3B, 4A or 4B) to penetrate into the other tubes when the tube unit 5 is detached from the main unit 1. When a soiled liquid dropping from the aspiration tube 2D runs along the wall surface and penetrates into the air feeding tube 3D or the water feeding tube 4D, it unnecessarily soils the air feeding tube 3D or the water feeding tube 4D undesirably from a hygienical viewpoint. Such soiling adds surplus works for cleaning and sterilizing the tube 3D or 4D.

When the tubes 2D, 3D and 4D of the example shown in FIG. 9 are disposed so as to protrude, however, a soiled water, etc. does not penetrate by way of a wall surface.

Further, rubber gaskets (O-rings) 32 are disposed as airtightness maintaining means on a protruding portion of the aspiration tube 17B of the tube unit 21, and back flow preventive valve-gaskets 33 which serve also for maintaining airtightness are disposed on portions of the other air feeding tube 18B and water feeding tube 19B which protrude from the wall surface F2 of the tube unit 21 as shown in FIG. 4.

Figure 6A:
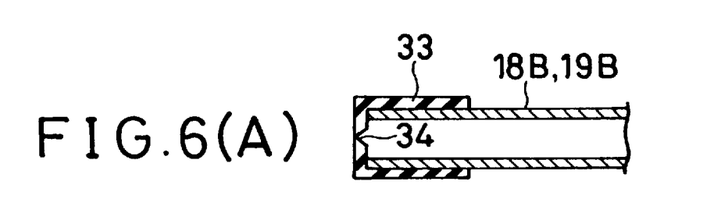
FIG. 6(A) is a side sectional view illustrating a back flow preventive valve-gasket for the air feeding tube or the water feeding tube shown in FIG. 4.
Figure 6B:
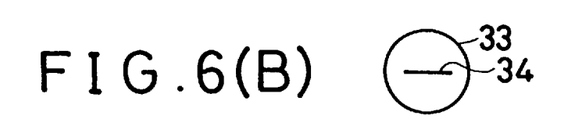
FIG. 6(B) is a front view of the gasket shown in FIG. 6(A)

Speaking more concretely, each of the back flow preventive valve-gaskets 33 has a form of a cylinder fitting over the air feeding tube 18B or the water feeding tube 19B and having a tip lid, and a cut 34 which has a sectional shape of V is formed in this lid as shown in FIGS. 6(A) and (B). This back flow preventing valve-gasket allows air and water to be fed out of the tube 18B or 19B under a predetermined pressure, but prevents air and water from flowing back from outside. Accordingly, this back flow preventive valve-gasket provides a merit to prevent soiled water, etc. from penetrating inside and leaking outside so far as a supply pressure is not applied.

Moreover, the first embodiment wherein the gaskets 32 and 33 for maintaining airtightness are disposed on the side of the tube unit 21 provides another merit that the gasket 32, the gasket 33 and their surroundings can be sterilized by performing sterilizing treatment of the tube unit 21 itself with an autoclave or the like.

Though length of the tubes on the side of the tube unit 21 is adjusted in the first embodiment described above, it is possible to configure the aspiration tube 17A so as to protrude longer than the other tubes 18A and 19A on the side of the control section 10C.

Second Embodiment

Figure 7A:
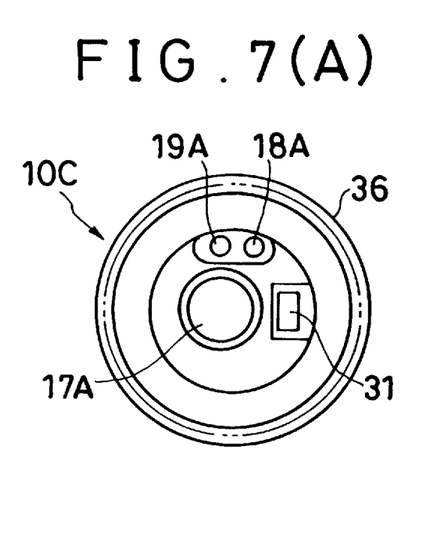
FIG. 7(A) is a front view of a control section exemplifying an arrangement of tubes used in a second embodiment of the present invention.
Figure 7B:
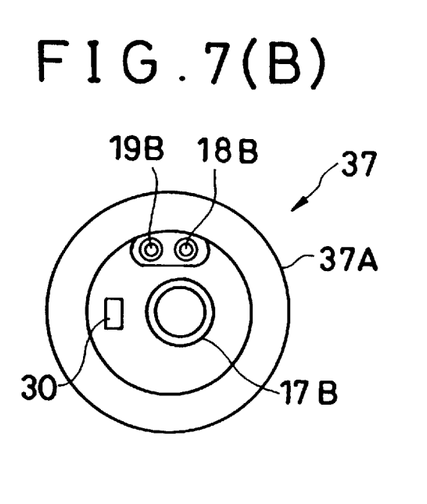
FIG. 7(B) is a front view of a tube unit used in the second embodiment of the present invention.

FIGS. 7(A) and 7(B) show a second embodiment wherein locations of tubes are modified. In the second embodiment, air feeding tubes 18A and 18B, and water feeding tubes 19A and 19B are arranged over aspiration tubes 17A and 17B in a faucet joint 36 of a control section 10C and a support portion 37A of a tube unit 37 as shown in the drawings. A side where control buttons 14A, 14B and 15 are disposed as shown in FIG. 1 is taken as an upper side. This arrangement provides a merit that it can prevent adhesion and penetration of a soiled liquid, etc. dropping from the aspiration tube 17A of the tube unit 37.

Third Embodiment

Figure 8:
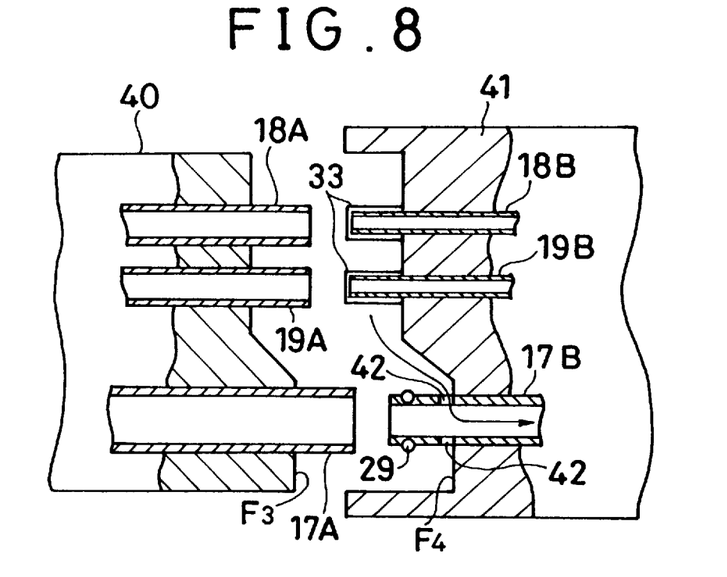
FIG. 8 is a sectional view exemplifying an arrangement of tubes in a third embodiment of the present invention.

FIG. 8 shows a third embodiment wherein protruding conditions of tubes are modified. In the third embodiment, tips of aspiration tubes are disposed at locations different from those of other tubes. Speaking concretely, an aspiration tube 17A is disposed on a convex surface F3 which is formed on a side of a control section 40, an aspiration tube 17B is disposed on a concave surface F4 which is formed on a side of a tube unit 41, and other tubes 18A, 18B, 19A and 19B are disposed as shown in FIG. 8, whereby tips of the aspiration tubes 17A and 17B are located differently from those of the other tubes in a direction along axes (arrangement) of the tubes. Further, an inlet hole 42 is formed in the foot (top or bottom) of a protruding portion of the aspiration tube 17B.

Such a structure wherein the tips of the aspiration tubes 17A and 17B are not aligned with those of the other tubes 18A, 18B, 19A and 19B in the direction along the axes of the tubes provides a merit to lower possibilities that liquid, etc. drop from the aspiration tubes 17A and 17B which aspirate soiled matters in particular onto the other tubes (when the tube unit 41 is set upside down and in other cases). Further, this structure wherein the aspiration tubes 17A and 17B are disposed below the other tubes also exhibits an effect to prevent penetration of a liquid dropping from the aspiration tubes 17A and 17B into the other tubes.

Furthermore, the inlet port 42 formed in the foot of the protruding portion of the aspiration tube 17B makes it possible to aspirate water, etc. flowing out of the upper water feeding tube 17B (or the air feeding tube 18B) into the aspiration tube 17B.

Though the three kinds of tubes are disposed in each of the embodiments described above, the present invention is applicable also to a coupler structure wherein any one or two kinds of aspiration tube 17, an air feeding tube 18 and a water feeding tube 19 are disposed.

As apparent from the foregoing description, the coupler structure according to the present invention wherein the aspiration tubes protrude longer than the other tubes allows the aspiration tubes to be pulled out last when the tube unit is detached, thereby being capable of preventing liquid, etc. remaining in the aspiration tubes from adhering to or penetrating into the other tubes. Further, the coupler structure according to the present invention provides a merit that it does not increase surplus cleaning and sterilizing works for the tubes which are originally to be not soiled so much.

Furthermore, the coupler structure according to the present invention wherein the tubes on the sides of the main unit and the tube unit are disposed so as to protrude from the wall surfaces and the protruding tubes are coupled with each other is capable of preventing soiled water, etc. flowing out of a tube from penetrating into the other tubes.

What is claimed is:

1. A coupler structure for tube units of endoscopes comprising:

an endoscope main unit in which various kinds of tubes including aspiration tubes are arranged;

a tube unit in which tubes to be connected to the tubes on the side of the main unit are arranged; and couplers which detachably couple the tubes on the side of said main unit to the tubes on the side of said tube unit, wherein said aspiration tubes for said coupler have protruding lengths longer than those of the other tubes so that said aspiration tubes are pulled out last when said tube unit is detached from said main unit.

2. A coupler structure for tube units of endoscopes according to claim 1, wherein a positioning member which restricts rotation and determines a position of the coupler is disposed in the coupler of said main unit or said tube unit, and this positioning member is longer than the tubes.

3. A coupler structure for tube units of endoscopes according to claim 1, wherein airtightness maintaining members for said coupler are disposed on the tubes on the side of said tube unit.

4. A coupler structure for tube units of endoscopes according to claim 1, wherein back flow preventive means is disposed in a tube of the coupler on the side of said tube unit.

5. A coupler structure for tube units of endoscopes comprising:

an endoscope main unit in which various kinds of tubes are arranged;

a tube unit in which tubes to be connected to the tubes on a side of said main unit are arranged; and couplers which detachably couple the tubes on the side of said main unit to the tubes on a side of said tube unit, wherein the tubes on the sides of said main unit and said tube unit are arranged so as to protrude from mounting wall surfaces in said couplers and protruding portions of the tubes are coupled with each other.

6. A coupler structure for tube units of endoscopes according to claim 5, wherein airtightness maintaining members for said coupler are disposed on the tubes on the side of said tube unit.

7. A coupler structure for tube units of endoscopes according to claim 5, wherein back flow preventive means are disposed over the tubes in the coupler on the side of said tube unit.

8. A coupler structure for tube units of endoscopes according to claim 5, wherein aspiration tubes and other tubes are disposed as said various kinds of tubes and protruding tips of the aspiration tubes are disposed at locations different from those of the other tubes in both of said couplers.

* * * * *